US012730118B2

(12) United States Patent
Keibel

(10) Patent No.: US 12,730,118 B2
(45) Date of Patent: Sep. 8, 2026

(54) METHOD FOR PERFORMING HEALTH TESTS AND MOBILE HEALTH TEST SYSTEM

(71) Applicant: KUKA Deutschland GmbH, Augsburg (DE)

(72) Inventor: Andreas Keibel, Augsburg (DE)

(73) Assignee: KUKA Deutschland GmbH (DE)

( * ) Notice: Subject to any disclaimer, the term of this patent is extended or adjusted under 35 U.S.C. 154(b) by 478 days.

(21) Appl. No.: 18/248,906

(22) PCT Filed: Oct. 14, 2021

(86) PCT No.: PCT/EP2021/078470
§ 371 (c)(1),
(2) Date: Aug. 30, 2023

(87) PCT Pub. No.: WO2022/079179
PCT Pub. Date: Apr. 21, 2022

(65) Prior Publication Data

US 2023/0400475 A1 Dec. 14, 2023

(30) Foreign Application Priority Data

Oct. 15, 2020 (DE) .................... 10 2020 213 038.8

(51) Int. Cl.
*G01N 35/00* (2006.01)
*A61B 10/00* (2006.01)
(Continued)

(52) U.S. Cl.
CPC ..... *G01N 35/0099* (2013.01); *A61B 10/0051* (2013.01); *A61B 10/0096* (2013.01);
(Continued)

(58) Field of Classification Search
CPC .... G01N 35/0099; G16H 40/67; G16H 40/20; G16H 10/40; G16H 50/80; G16H 80/00;
(Continued)

(56) References Cited

U.S. PATENT DOCUMENTS 8,965,583 B2 2/2015 Ortmaier et al.
2014/0108030 A1* 4/2014 Tejeda-Monteagut ........................ G06Q 10/1093 705/2
(Continued)

FOREIGN PATENT DOCUMENTS

CN 107704937 A 2/2018
CN 111481235 A 8/2020
(Continued)

OTHER PUBLICATIONS

European Patent Office; Search Report in related International Patent Application No. PCT/EP2021/078470 dated Feb. 16, 2022; 3 pages.
(Continued)

*Primary Examiner* — Truc M Do
(74) *Attorney, Agent, or Firm* — Dorton & Willis, LLP

(57) ABSTRACT

A mobile health system and method for performing health tests and for acquiring health-related personal data by a computer network and resources connected in the computer network. Communication means of the network include a health database having a database management system, a personal database, a plurality of mobile health test systems each having at least one automatically controllable robot that is designed and configured to perform a health-related test method, and a test system controller which is connected to the computer network via a first communication means. A plurality of terminals are connected to the computer network via second communication means.

15 Claims, 10 Drawing Sheets

(51) Int. Cl.

| | |
|---|---|
| ***A61L 2/22*** | (2006.01) |
| ***A61L 2/24*** | (2006.01) |
| ***G16H 10/40*** | (2018.01) |
| ***G16H 40/20*** | (2018.01) |
| ***G16H 40/67*** | (2018.01) |
| ***G16H 50/80*** | (2018.01) |
| *A61L 103/15* | (2026.01) |
| *G16H 80/00* | (2018.01) |

(52) U.S. Cl.
CPC .................. *A61L 2/22* (2013.01); *A61L 2/24* (2013.01); *G16H 10/40* (2018.01); *G16H 40/20* (2018.01); *G16H 40/67* (2018.01); *G16H 50/80* (2018.01); *A61L 2103/15* (2026.01); *G16H 80/00* (2018.01)

(58) Field of Classification Search
CPC ... A61B 10/0051; A61B 10/0096; A61L 2/22; A61L 2/24; A61L 2202/24
See application file for complete search history.

(56) References Cited

U.S. PATENT DOCUMENTS

| | | | | |
|---|---|---|---|---|
| 2017/0032092 | A1* | 2/2017 | Mink | G06Q 30/0241 |
| 2018/0263703 | A1 | 9/2018 | Pinter et al. | |
| 2019/0041854 | A1 | 2/2019 | Millhouse | |
| 2019/0242916 | A1* | 8/2019 | Guarracina | B25J 15/04 |
| 2019/0331701 | A1* | 10/2019 | Polley | G01N 35/0099 |
| 2020/0198142 | A1* | 6/2020 | Lai | B25J 9/1676 |
| 2020/0338309 | A1 | 10/2020 | Kopperschmidt et al. | |

FOREIGN PATENT DOCUMENTS

| | | | |
|---|---|---|---|
| CN | 111631754 | A | 9/2020 |
| DE | 102017201437 | A1 | 8/2018 |
| DE | 102017220500 | A1 | 5/2019 |
| EP | 2214872 | B1 | 2/2019 |
| WO | 2019175675 | A2 | 9/2019 |

OTHER PUBLICATIONS

German Patent Office; Examination Report in related German Patent Application No. 10 2020 213 038.8 dated Jul. 7, 2021; 11 pages.

Chinese Patent Office; Office Action in related Chinese Patent Application No. 2021800842239 dated Jul. 17, 2025; 9 pages.

* cited by examiner

METHOD FOR PERFORMING HEALTH TESTS AND MOBILE HEALTH TEST SYSTEM

CROSS-REFERENCE TO RELATED APPLICATIONS

This application is a national phase application under 35 U.S.C. § 371 of International Patent Application No. PCT/EP2021/078470, filed Oct. 14, 2021 (pending), which claims the benefit of priority to German Patent Application No. DE 10 2020 213 038.8, filed Oct. 15, 2020, the disclosures of which are incorporated by reference herein in their entirety.

TECHNICAL FIELD

The invention relates to a method for performing health tests and collecting health-related personal data by a computer network and resources connected in the computer network. The invention also relates to an associated mobile health test system.

BACKGROUND

EP 2 214 872 B1 describes a method for projecting an image onto the surface of an object, comprising the method steps of projecting an image onto the surface of an object, which is a living being, by means of a device for projecting an image, which is in particular integrated in a robot arm of a robot or fastened to the robot arm taking an image of the image projected on the surface of the living being by means of a camera fastened to the robot arm or integrated in the robot arm, wherein the projected image represents virtual input means, and analyzing a further image data set associated with the image taken by the camera for a gesture of a person in order to recognize an actuation of the virtual input means.

SUMMARY

The object of the invention is to create a method for performing health tests and for collecting health-related personal data, as well as an associated mobile health test system, with which health tests can be performed as comprehensively as possible, at least to a large extent automatically, with little use of specialist personnel.

According to the invention, the object is solved by a method for performing health tests and for collecting health-related personal data, by means of a computer network and resources connected in this computer network via communication means, comprising

- a health database with a database management system and a personal database,
- a plurality of mobile health test systems, each having at least one automatically controllable robot which is designed and configured to perform a health-related test method, and a test system controller which is connected to the computer network via a first communication means, and
- a plurality of terminal devices that are connected to the computer network via second communication means, having the steps of:
- capturing personal data comprising personal location information entered through individuals' terminal devices in the health database by means of the database management system,
- as a function of a spatial accumulation of personal location information of several persons who have entered their personal location information via the terminal devices, providing one of the several mobile health test systems in spatial proximity of the location information,
- automatically sending information about an individualized location appointment for the person in question to the person's individual terminal device,
- configuring the provided mobile health test systems to perform the health-related test method on the individual to whom the individualized site visit is assigned during the scheduled time period of the individualized site visit,
- performing a laboratory diagnostic method to collect individualized test results from the individual health-related test methods,
- storing the individualized test results in the form of health-related personal data in the personal database of the health database by means of the database management system.

The invention thereby also comprises a concept for highly autonomous collection of infection data in the population by setting up decentralized mobile health test systems, in particular temporarily, where large numbers of individual citizens, i.e. persons, can sequentially each leave a sample, such as a throat swab or a nasal swab, for further analysis. The concept further provides for an Internet-based server system to arrange and organize the sample collection and to manage the procedures of the evaluation. Part of the concept is also the fastest possible provision of the test results for each individual person, but also for politics, public authorities, administration and the public health system, particularly in anonymized form. In this respect, the personal database can also be designed to store the data in anonymized form.

For example, the mobile health test systems may consist of a weatherproof enclosure that can be approached on one side by a car or van. On this side is a closable opening from which a robot can interact with the person or subject.

Inside the system there is the robot, a cleaning system, at least one camera, for example for recording the throat area of the test person, a storage area which can be loaded from the outside through a separate flap if necessary. For example, a refrigerator for the samples taken, which can be opened and closed by a simple mechanism, may also be present.

The inventive system prevents infection of other person and reduces the manpower required to collect the test results. In principle, any medical test methods can be used for the health tests. The specific medical test method to be used in each case depends on the current specific infection event or the type of infecting germs. By performing the test method automatically by means of at least one robot, infection of other persons by an infected person is prevented. The automated test method can also be performed anonymously, i.e. any person who wishes to be tested can do so without having to communicate or contact anyone else about it. The inventive system can be used around the clock, as 24 hours a day, in particular also seven days a week. Medically qualified personnel do not have to be called upon to perform health tests in this manner, which means that these capacities, for example in hospitals, can be maintained or even expanded there.

By collecting personal data, which comprise personal location information and which have been entered via the terminal devices of individuals, in the database of the health database by means of the database management system, the system determines in which regions of a country there is currently a particularly high demand for the performance of health tests. Mobile health test systems can then be made available on site as needed. The mobile health test systems can be dropped off at suitable locations, such as public places, parking lots or similar, for example, by means of trucks.

Each person can independently reserve, or agree upon and be assigned, a specific time at which the person should arrive at a specific mobile health test system. The collected data can be anonymized or personalized. In the case of personalized data, this may comprise, for example, the name, address and contact details, such as telephone number or e-mail address. In the case of anonymized data, the person concerned can arrange a time or an appointment without providing personalized data. The person can be assigned a code by means of a random algorithm. The code can be assigned, for example, in plain text as a combination of letters and/or numbers, or encoded, for example, in the form of a bar code or a QR code.

As a function of a spatial clustering of personal location information of a plurality of individuals who have entered their personal location information via the terminal devices, providing one of the plurality of mobile health test systems is performed in spatial proximity to the personal location information of the plurality of individuals.

The system automatically sends information about an individualized location appointment for the person to the person's individual terminal device. The automatic sending of information about an individualized location appointment for the person in question can take place simply by sending a confirmation to the person who has searched for and selected an individualized location appointment online from a set of available free location appointments.

In due course, configuring the provided mobile health test apparatus to perform the health-related test method on the individual to whom the individualized site visit is assigned occurs during the scheduled time period of the individualized site visit. Of course, the apparatus provided for mobile health test systems to perform the health-related test method on individuals can be configured in advance in time, even before one or more individuals are given individualized site visits. For example, it may be envisaged that mobile health test systems are made available and configured at an early stage at certain "hotspots", as an accumulation of necessary health tests can be assumed there.

Performing a laboratory diagnostic method to collect individualized test results from the individual health-related test methods may already take place within the mobile health test system, if applicable. Alternatively or complementarily, performing a laboratory diagnostic method to collect individualized test results from the individual health-related test methods can be performed separately to the mobile health test systems, for example, in inpatient laboratories, hospitals, or health centers. This may depend on the type of laboratory diagnostic method required in each individual case of infectious disease. If necessary, rapid tests can thus already be performed within the mobile health test system and the result communicated to the respective tested person immediately on site.

Moreover, the individualized test results are then stored in the form of health-related personal data in the personal database of the health database by means of the database management system. The health-related personal data and the personal database can be anonymized or personalized. For example, there may be a first database that contains only anonymized health-related personal data and there may be a second database that contains only personalized health-related personal data. Personal data is generally understood to be all data that is obtained from an individual person, regardless of whether it is anonymized or personalized. For example, a substantial health-related personal record is the test result of the health test performed. For example, this particular person record can be only one of the two states "positive" or "negative" or "0" or "1".

The mobile health test system can be designed to be independently mobile by means of a chassis and wheels, for example. Alternatively, the mobile health test system may be transportable by means of a separate vehicle, such as a truck, particularly a semitrailer or trailer of a truck. For example, the mobile health test system may be designed in the form of a transportable container.

A counter area of the mobile health test system may have a window opening that may be closable by means of a flap. In the open state of the flap, an input terminal and an output terminal are accessible to the person. For example, the person can drive up to the mobile health test system in their own vehicle and authorize themselves at the input terminal. Alternatively, the person may arrive at the mobile health test system on foot or, for example, by bicycle. Such authorization can be done, for example, by entering an individual access code on a keyboard of the input terminal. Alternatively, authorization can be performed in a non-contact manner, for example, using a camera to automatically identify the person, for example, by facial recognition or by recognizing an access code held in the camera's field of view, such as an individual bar code or QR code. The individual access code can be obtained by the person, as part of the registration and assignment of an individual site appointment, when the person registers for the individual test appointment, for example, online via their own mobile terminal device. For example, the person can hold an access code shown on the display of their mobile terminal device into the camera so that the access code can be captured automatically. Alternatively, the access code may be available as an email printout, for example, wherein the person can then hold the printout up to the camera.

For example, the output terminal may comprise a screen and/or a speaker to provide information and/or instructions to the person.

The test system controller may be designed and configured to automatically perform a personal authorization of the individual at the health test system based on data from the health database before the individual health-related test method is performed on that individual at the health test system. The individual health-related test method described below includes taking a nasal swab or throat swab from the person's oral cavity. However, the health-related test method according to the invention may also comprise additional tests, such as also a fever measurement, blood pressure measurement, pulse measurement, breath sound measurement, blood glucose measurement, and/or similar. To this end, the test facility may comprise, for example, a lockable or releasable chamber into which both the robotic arm has access and the person can insert a body part, such as a head, hand, or arm, so that the robotic arm can test the particular body part inserted into the chamber.

For example, the robot can be automatically controlled by the test system controller in such a manner that the robot first automatically removes a single-sample container from a container store and automatically inserts it into a holder. Subsequently, the robot can be automatically controlled by the test system controller in such a manner that the robot automatically removes a new, sterile sample carrier from a sample carrier storage and, while continuously monitoring, for example, the oral cavity of the person by means of the camera, automatically inserts the sample carrier into the oral cavity of the person, for example, by means of a force/torque-controlled robot, in order to remove the sample from the oral mucosa and/or the pharynx of the person. The robot can also be controlled to automatically insert the sample carrier into the person's nose, for example by means of a force/torque controlled robot, while continuously monitoring, for example, the person's nasal passages by means of the camera, to collect the sample from the person's nasal mucosa.

Alternatively, it can also be provided that the robot merely hands the sample carrier to the person automatically, such that the person independently takes a sample from their nose, from their oral mucosa and/or from their throat by means of their own hand, for example in accordance with instructions displayed visually and/or explained acoustically via the output terminal as to the manner in which the sample collection must be performed if the sample collection is performed manually. For example, the person can choose at the input terminal whether they agree to automated sample collection by means of the robot, or whether they would prefer to perform the sample collection manually themselves. When booking an appointment, the person can, if necessary, determine in advance whether they agree to automated sample collection by means of the robot, or whether they would prefer to perform the sample collection manually themselves. To do this, the person can be shown instructions on how each sample collection would be performed while booking the appointment, making the decision easier for the person.

In both cases, the sample carrier is subsequently inserted automatically by the robot into the individual sample container together with the removed sample, and the individual sample container is sterilely sealed. The robot then automatically removes the sealed individual sample container with the sample carrier and sample contained therein from the holder and stores it in a sample collector. For example, the sample collector may be automatically height-adjustably stored within the mobile health test system such that the sample collector can be automatically moved from its storage position to a pick-up position where the robot can automatically store the sealed single sample container with the sample carrier and sample contained therein in the sample collector.

The sample collector can be picked up from the mobile health test system by means of a transport unit, such as a vehicle, and brought, for example, in batches to the stationary laboratory, where a laboratory diagnostic method can be performed on the samples, also in an automated manner.

After an individual health test has been performed on the person, the robot can be disinfected by means of a disinfection device. For this purpose, the disinfection device can have a supply of disinfectant which can be automatically applied to the robot by means of spraying apparatus. The disinfection device can, for example, be automatically height-adjustably stored within the mobile health test system in such a manner that the disinfection device can be automatically moved from its storage position to a treatment position where the robot can be sprayed with disinfectant, particularly completely, but at least the relevant components.

The database management system may be configured to automatically notify the individual person of their individualized test results via one of the second means of communication and/or automatically send anonymized data from multiple test results from multiple persons to a statistical database connected to the database management system via third means of communication.

The individualized test results can be communicated to the respective person, for example, by e-mail, via an app of a smartphone, a smartwatch or also in writing by mail to a specified address, in particular sent automatically.

For example, the statistics database may only have reduced data sets that can no longer be individually assigned to specific persons. However, these may contain generalized information, such as data on the location of positively tested individuals or the ratio of positively tested individuals to negatively tested individuals. The statistical database may be configured to be accessible to policymakers, public officials, administrators, and the public health system.

The at least one automatically controlled robot may be controlled by the test facility controller such that the robot automatically performs the health-related test method.

The health-related test method may comprise a swab from a person's throat or oral cavity or a swab from the person's nose by means of a sterile sample carrier, wherein, in a particular embodiment, the sterile ample carrier is automatically guided by the robot of the mobile health test system under the control of the test system controller in a force/torque-controlled operation of the robot. In this context, the test system control can also be supported by AI-assisted image processing in order to identify the locations to be approached, where the sample collection by means of the sterile sample carrier should best take place, in the individual person.

In the health-related test method, a person's throat or oral cavity can be optically captured by a camera, for example. From the optically captured images or video sequences, those areas within the person's pharynx or oral cavity can be identified, particularly in real time, which are to be scanned by the head of the sample carrier. The robot can be assisted in its movements by artificial intelligence systems. If necessary, these can analyze the noses, nasal cavities, pharynxes, and oral cavities of a wide variety of individuals and determine the appropriate locations to palpate the sample carrier's head. If necessary, the robot can be controlled in a compliant manner in order to prevent any injuries.

The test system controller may be designed and configured to temporarily store a plurality of samples of tested individuals obtained during performed health-related test methods, individually assigned, in a sample magazine of the mobile health test system, for batch collection of the plurality of samples from the mobile health test system for transport of the plurality of samples to a stationary laboratory that performs a laboratory diagnostic method on each of the plurality of samples.

The test system controller may be designed and configured to automatically perform a health test and/or laboratory diagnostic method in the health test system by means of the robot.

The test system controller may be designed and configured to automatically perform a personal authorization of the individual at the health test system based on data from the health database before the individual health-related test method is performed on that individual at the health test system.

The object is also solved by a mobile health test system, comprising a counter area which is configured such that persons can contact apparatuses of the mobile health test system, wherein the apparatuses comprise at least one input terminal and at least one output terminal, further comprising at least one automatically controllable robot which is designed and configured to automatically perform at least a substep of a health-related test method on a person and a test system controller comprising a transmitting and receiving apparatus designed to connect the test system controller to a computer network via a first communication means in such a manner that, in a connected state, personal data can be retrieved from a personal database of the health database via the computer network to which a health database is connected and can be written to the personal database, wherein the test system controller is designed and configured to perform a health-related test method, taking into account the personal data, on a person located in the counter area of the mobile health test system, using the at least one substep automatically performed by the at least one robot during the performance of the health-related test method.

The mobile health test system may have a disinfection device designed and configured to disinfect the at least one robot of the mobile health test system.

The mobile health test system may have an audio and/or video communication interface designed and configured to enable communication between a person located in the counter area of the mobile health test system and a service person located remotely from the mobile health test system.

If a person is very unsure of how to use the mobile health test system, the person may request assistance from a human by means of a “help” input means. Support is preferably provided online, i.e. on a virtual, or telecommunicative basis. Thus, the supporting person is not available on site, but communicates with the requesting person remotely. In the case of medically relevant problems or questions, the service person may be, for example, a physician or a physician’s assistant. Alternatively, in the event of technical problems or questions, for example, the service person may be a technician who is familiar with the operation of the mobile health test system.

Specific embodiments of the invention are explained in more detail in the following descriptions with reference to the accompanying figures. Specific features of these embodiments, possibly considered individually or in further combinations, can represent general features of the invention, regardless of the specific context in which they are mentioned.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
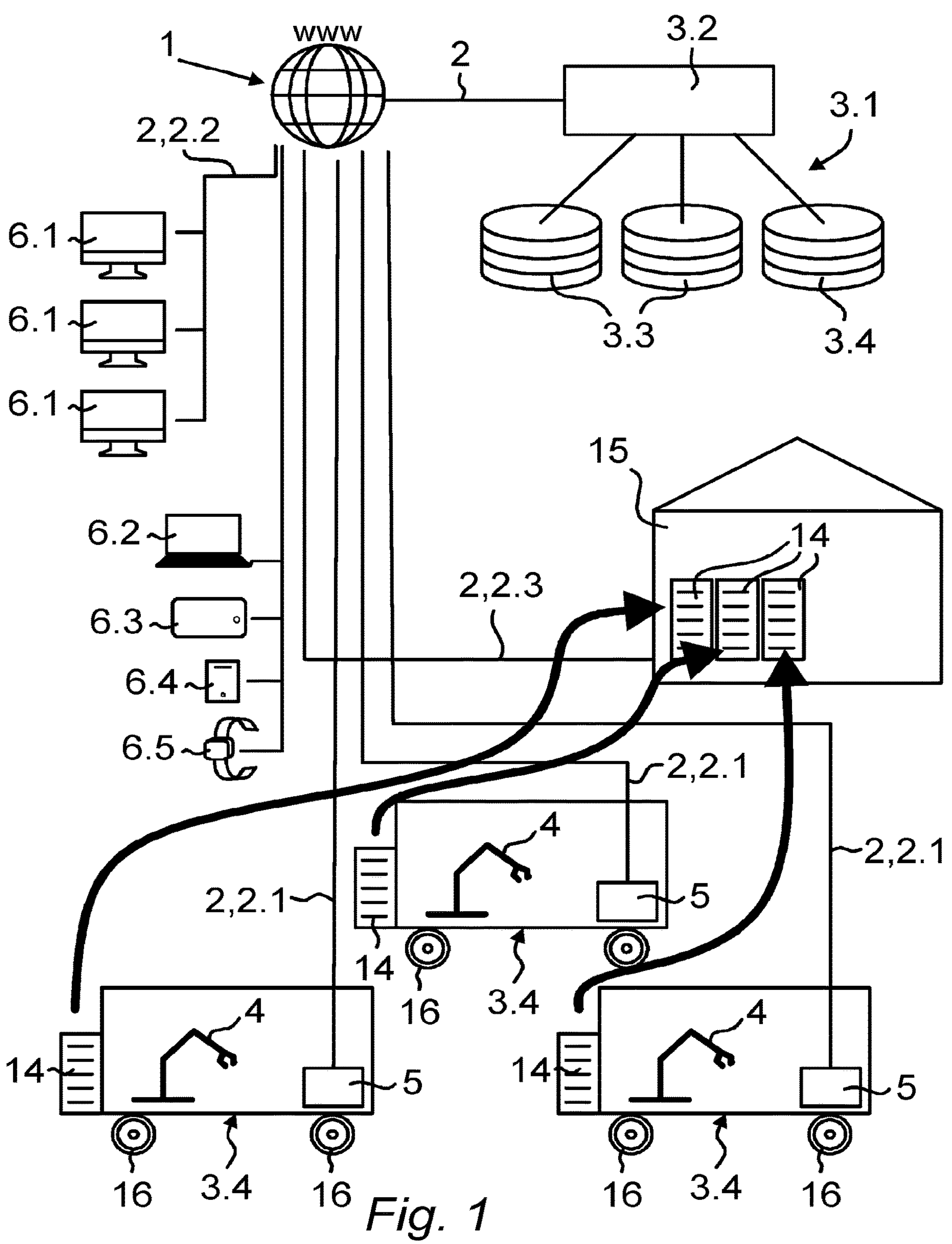
FIG. 1 shows a schematic diagram of an exemplary system for performing health tests and collecting health-related personal data, by means of a computer network and resources connected in this computer network via communication means.

In accordance with FIG. 1, a computer network 1, such as the Internet, is used in the application of the method for performing health tests and collecting health-related personal data, as well as resources 3 connected in this computer network 1 via communication means 2.

In the case of the present embodiment, the resources 3 comprise a health database 3.1 with a database management system 3.2 and at least one personal database 3.3. The resources 3 further comprise a plurality of mobile health test systems 3.4 each comprising at least one automatically controllable robot 4 designed and configured to perform a health-related test method, and a test system controller 5 connected to the computer network 1 via a respective first communication means 2.1. The resources 3 also comprise a plurality of terminal devices 6, each of which is connected to the computer network 1 via second communication means 2.2. The terminal devices 6 can be any number and types of devices from the group of stationary computers 6.1, mobile computers 6.2, such as notebooks or ultrabooks, tablet computers 6.3, smartphones 6.4, and smartwatches 6.5.

Figure 2:
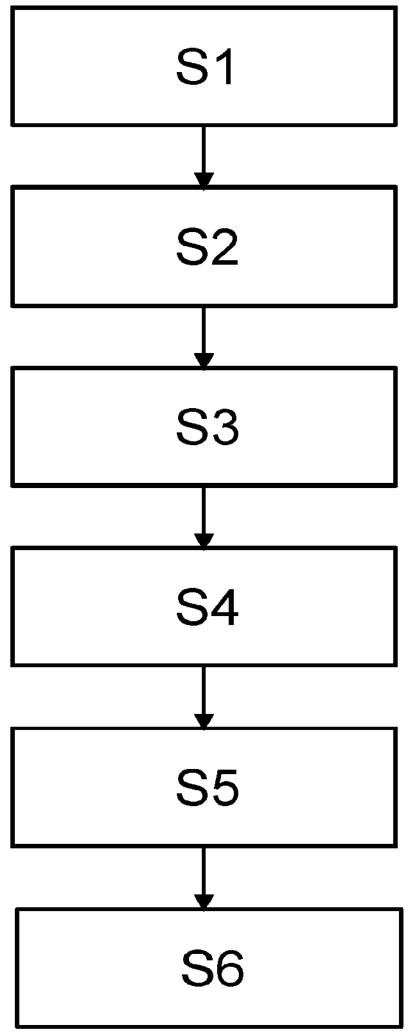
FIG. 2 shows a flow chart of the steps in the basic inventive method.
Figure 3:
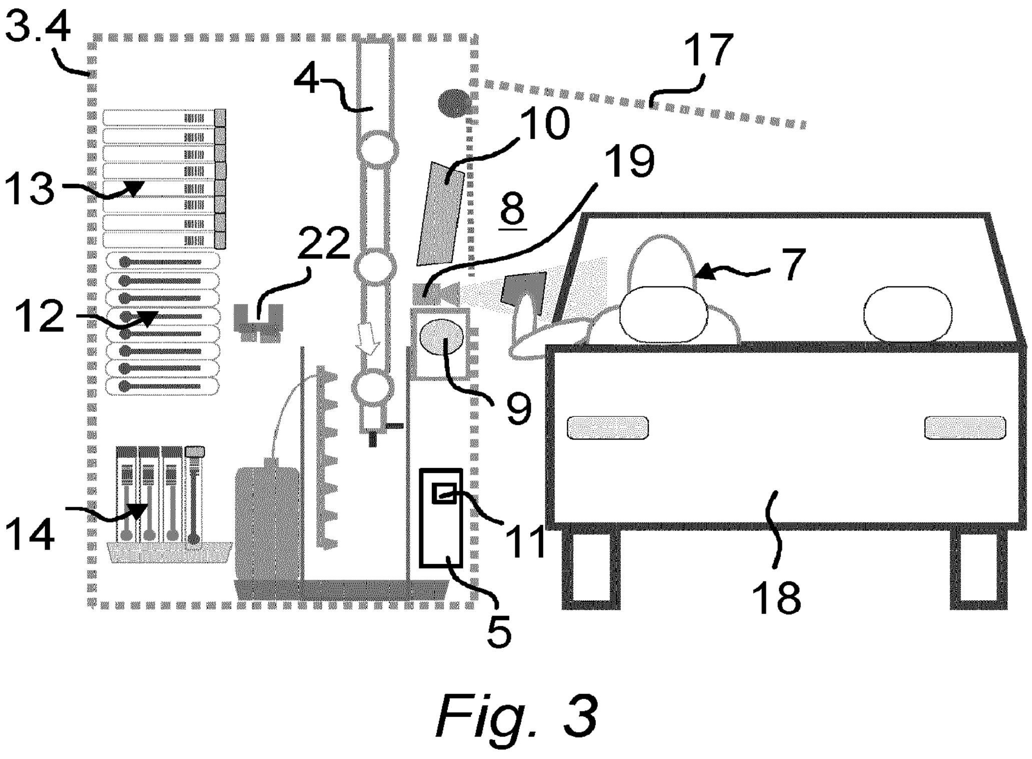
FIGS. 3 to 16 show schematic diagrams of an exemplary embodiment of a mobile health test system, in various states of embodiment, which can occur when performing the inventive method.

As illustrated in FIG. 2, the method has the following steps:

In a first step S1, a collection of personal data comprising personal location information entered via the terminal devices 6 of persons 7 is performed in the database 3.3 of the health database 3.1 by means of the database management system 3.2.

In a second step S2, one of the plurality of mobile health test systems 3.4 is provided in spatial proximity to the personal location information, in response to a spatial clustering of personal location information of a plurality of individuals 7 who have entered their personal location information via the terminal devices 6.

In a third step S3, information about an individualized location appointment for the person 7 in question is automatically sent to the individual terminal device 6 of the person 7.

In a fourth step S4, the provided mobile health test apparatuses 3.4 are configured to perform the health-related test method on the person 7 to whom the individualized site visit is assigned, in the scheduled time period of the individualized site visit.

In a fifth step S5, a laboratory diagnostic method is performed to collect individualized test results from the individual health-related test methods.

In a sixth step S6, the individualized test results are stored in the form of health-related personal data in the personal database 3.3 of the health database 3.1 by means of the database management system 3.2.

The database management system 3.2 may be configured to automatically notify the individual person 7 of their individualized test results via one of the second communication means 2.2 and/or to automatically send anonymized data from multiple test results of multiple persons 7 to a statistical database 3.4 connected to the database management system 3.2 via third communication means 2.3.

The second communication means 2.2 can be fixed network Internet connections or wireless communication connections, for example in a mobile network.

As illustrated in the schematic diagrams of FIG. 3 to FIG. 16 in an exemplary embodiment of a mobile health test system, in various embodiment states that can occur during the performance of the method according to the invention, the at least one automatically controlled robot 4 can be controlled accordingly in each case by the test system controller 5 in such a way that the robot 4 automatically performs the health-related test method.

The exemplary mobile health test system 3.4 in accordance with FIG. 3 to FIG. 16, has a counter area 8 designed in such a manner that persons 7 can contact apparatuses of the mobile health test system 3.4, wherein the apparatuses comprise at least one input terminal 9 and at least one output terminal 10. The mobile health test system 3.4 further has the at least one automatically controllable robot 4 that is designed and configured to automatically perform at least a substep of a health-related test method on a person 7.

The mobile health test system 3.4 further comprises the test system controller 5, which comprises a transmitting and receiving device 11 designed to connect the test system controller 5 to the computer network 1 via the first communication means 2.1 in such a manner that, in a connected state, personal data can be retrieved from a personal database 3.3 of the health database 3.2 via the computer network 1 to which the health database 3.2 is connected and written to the personal database 3.3.

The test system controller 5 is designed and configured to perform a health-related test method taking into account personal data on a person 7 located in the counter area 8 of the mobile health test system 3.4, using the at least one sub-step automatically performed by the at least one robot 4 during the performance of the health-related test method.

Figure 7:
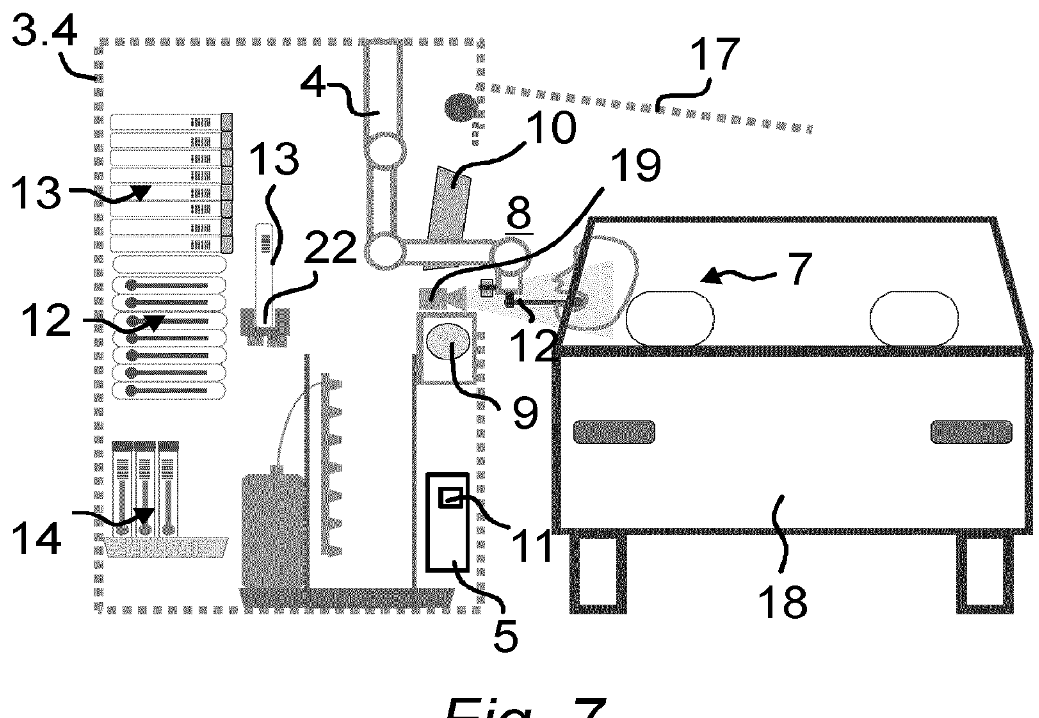

The health-related test method may comprise, for example, a swab from the pharynx or oral cavity of a person 7 by means of a sterile sample carrier 12, wherein the sterile sample carrier 12 is automatically guided by the robot 4 of the mobile health test system 3.4, as illustrated, for example, in FIG. 7, controlled by the test system controller 5, in particular in a force/torque-controlled operation of the robot 4.

In the case of the present embodiment, the test system controller 5 is designed and configured to individually allocate a plurality of samples 12*a* of the tested persons 7 obtained during performed health-related test methods, for example via individual sample containers 13 having information about the respective tested person 7, in a sample magazine 14 of the mobile health test system 3.4, for batchwise collection of the plurality of samples 12*a* from the mobile health test system 3.4 for transportation of the plurality of samples 12*a* to a stationary laboratory 15 (FIG. 1), which performs a laboratory diagnostic method on each of the plurality of samples 12*a*.

In the case of the present embodiment, the test system controller 5 is designed and configured to automatically perform a health test in the health test system 3.4 by means of the robot 4. For example, such health tests can be performed as described below.

The mobile health test system 3.4 can be designed to be independently mobile, for example, by means of a chassis and wheels 16. Alternatively, the mobile health test system 3.4 can be transportable by means of a separate vehicle, such as a truck, particularly a trailer or semitrailer of a truck. For example, the mobile health test system 3.4 can be designed in the form of a transportable container.

The counter area 8 of the mobile health test system 3.4 may have a window opening, which may be closable by means of a flap 17. In the open state of the flap 17, the input terminal 9 and the output terminal 10 are accessible to the person 7. For example, the person 7 may drive up to the mobile health test system 3.4 in their own vehicle 18 and authorize themselves at the input terminal 9. Such authorization can be performed, for example, by entering an individual access code at a keyboard of the input terminal 9. Alternatively, authorization can be performed in a non-contact manner, for example, using a camera 19 to automatically identify the person 7, for example, by facial recognition or by recognizing an access code held in the camera's 19 field of view, such as an individual bar code or QR code. The individual access code can be obtained by the person, as part of the registration and assignment of an individual site appointment, when the person 7 registers for the individual test appointment, for example, online via their own mobile terminal device 6.2 to 6.5. For example, the person 7 can hold an access code shown on the display of their mobile terminal device 6.2 to 6.5 into the camera 19 so that the access code can be captured automatically. Alternatively, the access code may be available as an email printout, for example, wherein the person 7 can then hold the printout up to the camera 19.

For example, the output terminal 10 may comprise a screen and/or a speaker to provide information and/or instructions to the person 7.

The test system controller 5 may thus be designed and configured to automatically perform a personal authorization of the person 7 at the health test system 3.4 based on data from the database 3.3 of the health database 3.1, before the individual health-related test method is performed on this person 7 at the health test system 3.4. In the following, the taking of a throat swab from the oral cavity 20 of the person 7 is described as an individual health-related test method.

Figure 4:
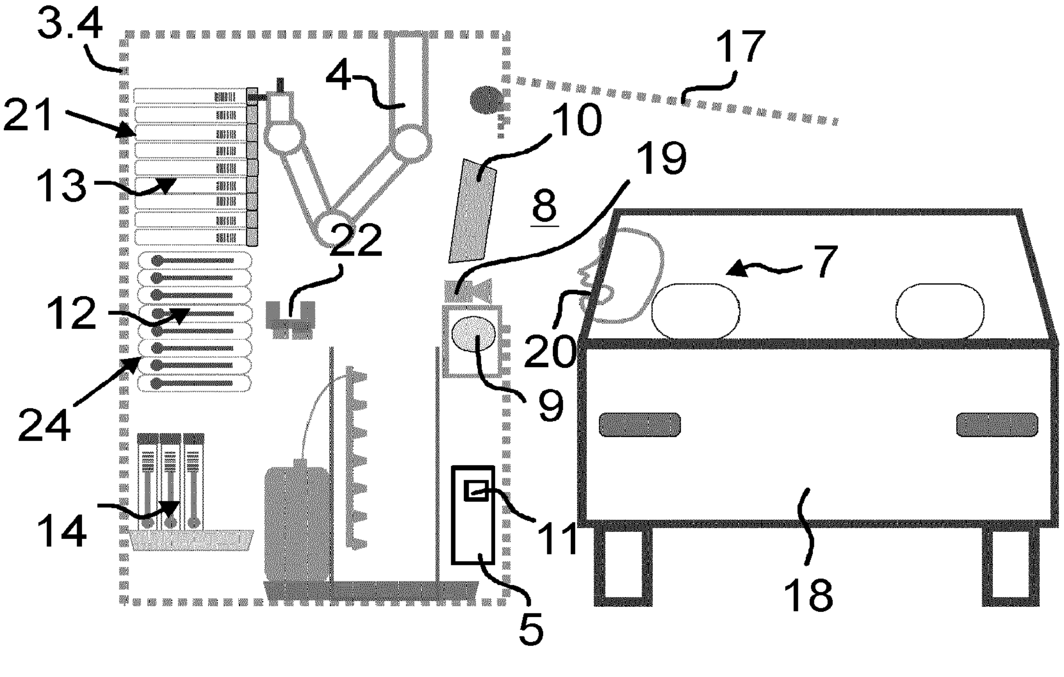
Figures 5, 6:
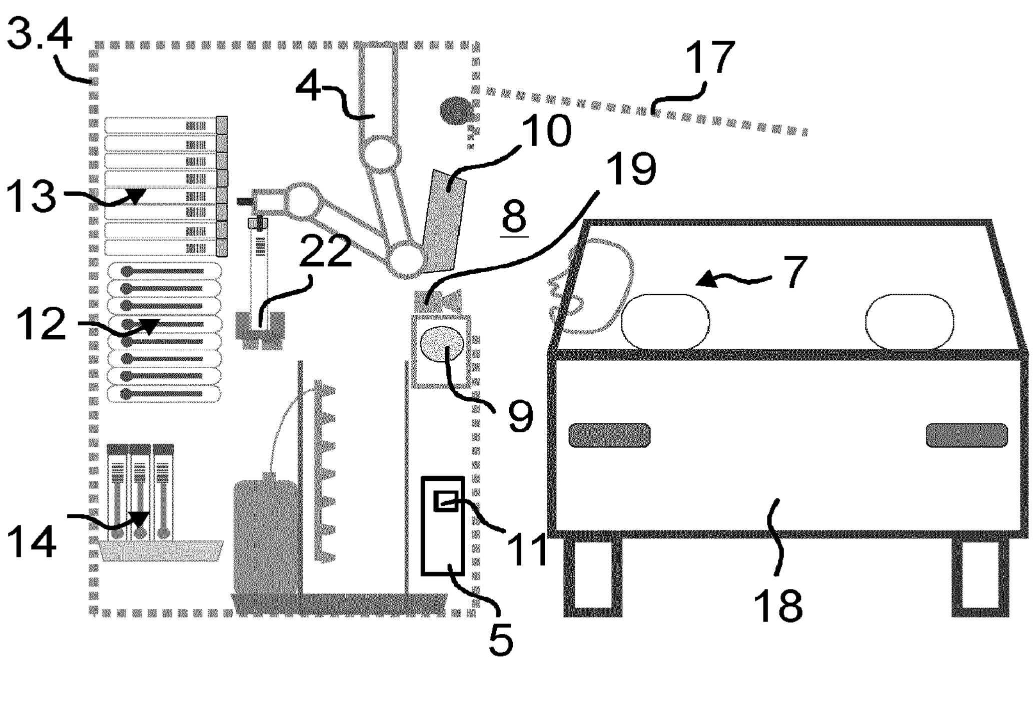
Figure 8:
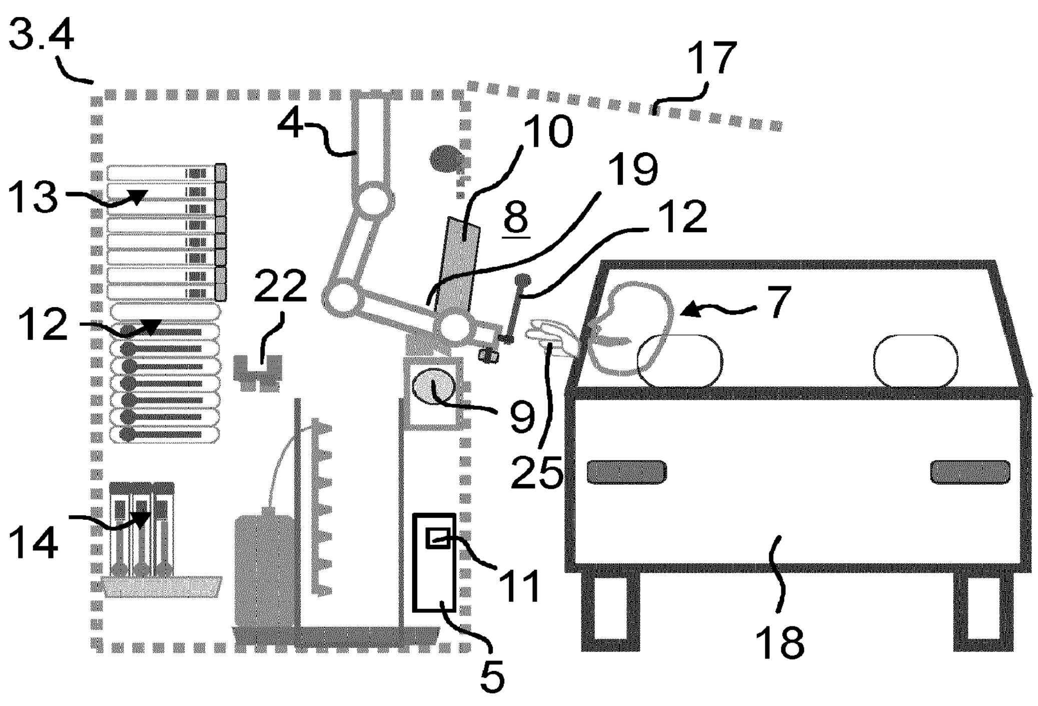
Figure 9:
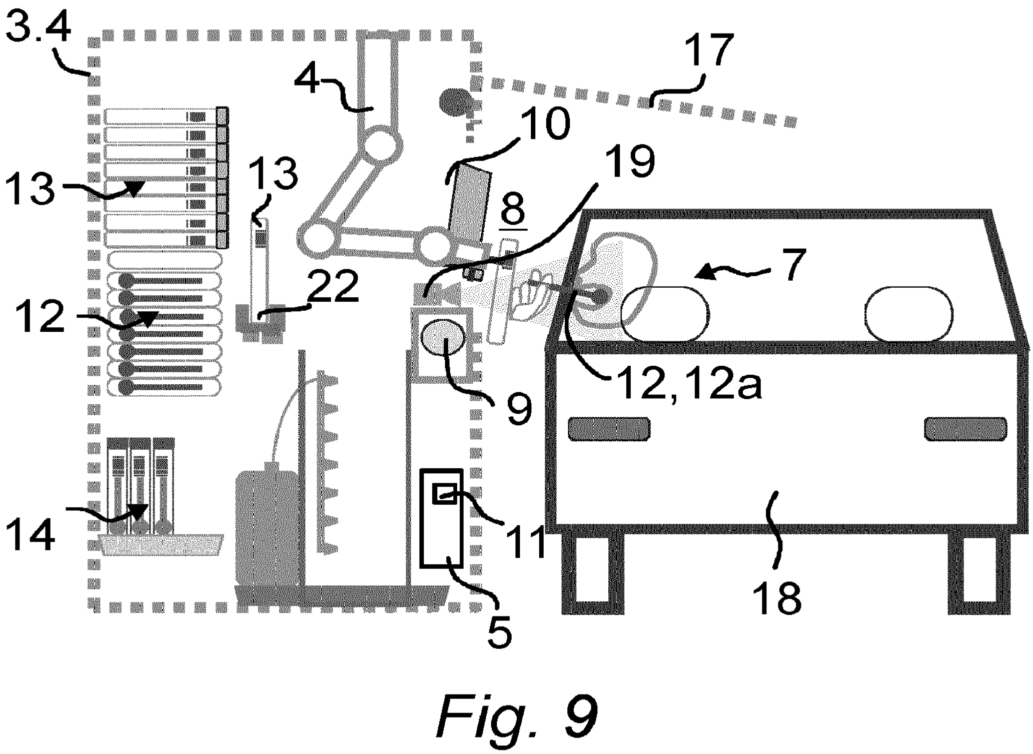

As illustrated in FIG. 4, the robot 4 can be automatically controlled by the test system controller 5 in such a manner that the robot 4 first automatically removes a single sample container 13 from a container store 21 and automatically inserts it into a holder 22, as shown in FIG. 5. Subsequently, the robot 4 can be automatically controlled by the test system control 5 in such a manner that the robot 4 automatically removes a new, sterile sample carrier 12 from a sample carrier storage 23, as shown in FIG. 6 and, while continuously monitoring the oral cavity 20 of the person 7 by means of the camera 19, automatically inserts the sample carrier 12 into the oral cavity 20 of the person 7, for example by means of a force/torque-controlled robot 4, in order to remove the sample 12*a* from the oral mucosa and/or pharynx of the person, as indicated in FIG. 7. Alternatively, as illustrated in FIG. 8, it can also be provided that the robot 4 merely hands the sample carrier 12 automatically to the person 7, such that the person 7 independently takes a sample 12*a* from their oral mucosa and/or throat by means of their own hand 25, for example in accordance with instructions displayed visually and/or explained acoustically via the output terminal 10 as to the manner in which the sample taking must be performed if the sample taking is performed manually. For example, at the input terminal 9, the person 7 can choose for themselves whether they agree to automated sample collection by means of the robot 4, or whether they would prefer to perform the sample collection manually themselves, as is also shown in FIG. 9.

Figure 10:
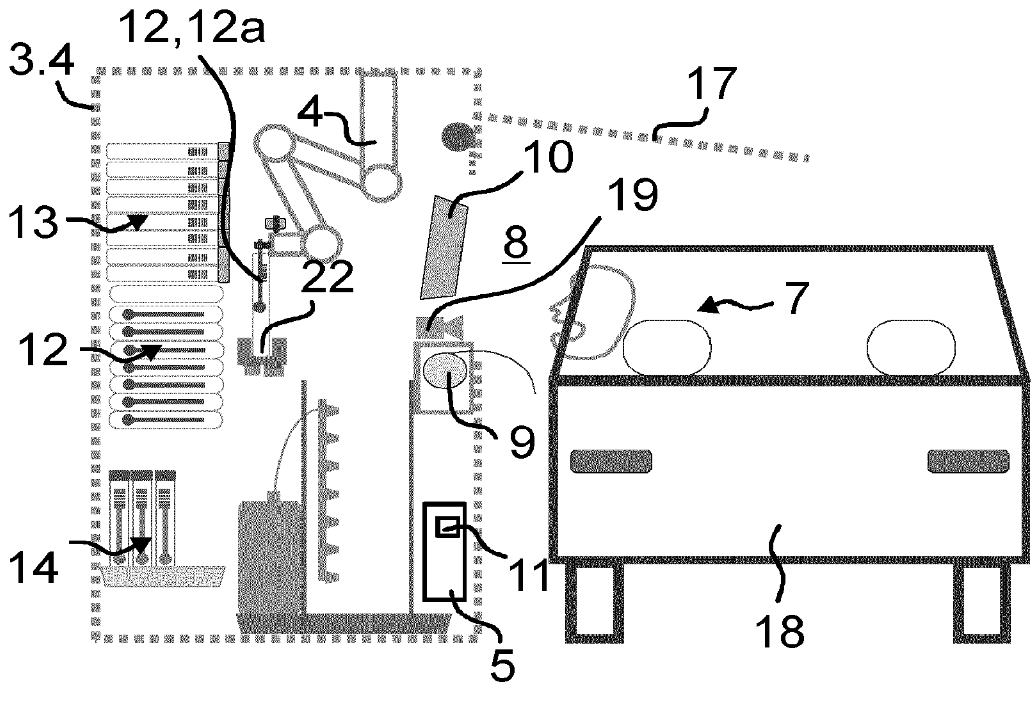
Figure 11:
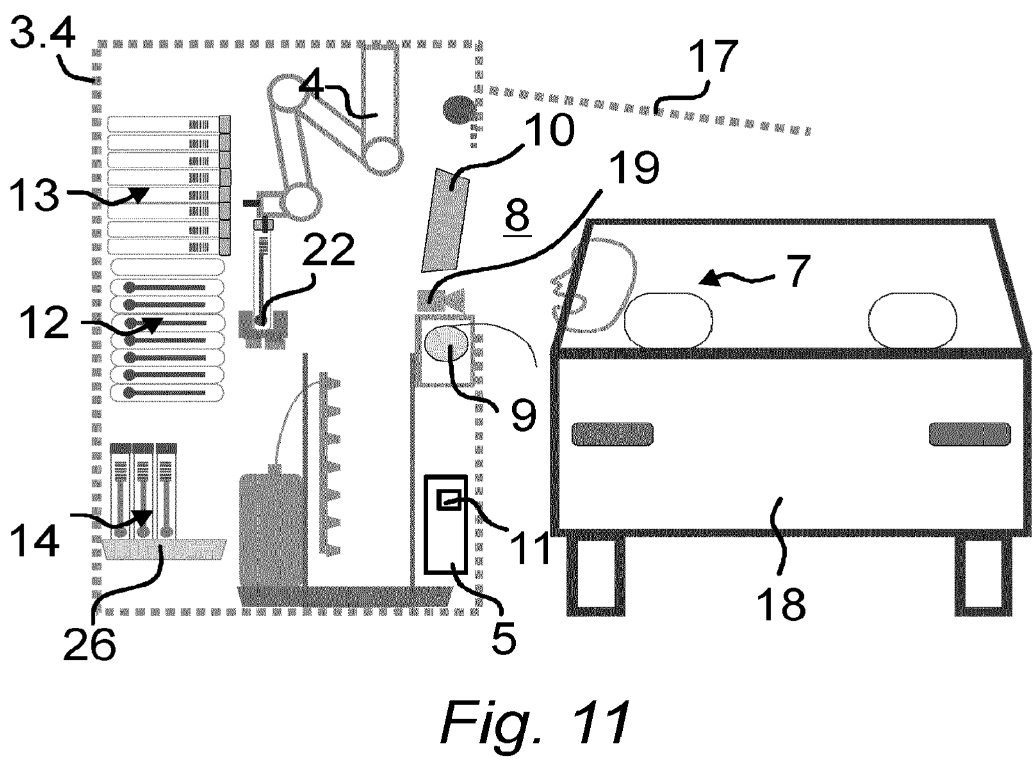
Figure 12:
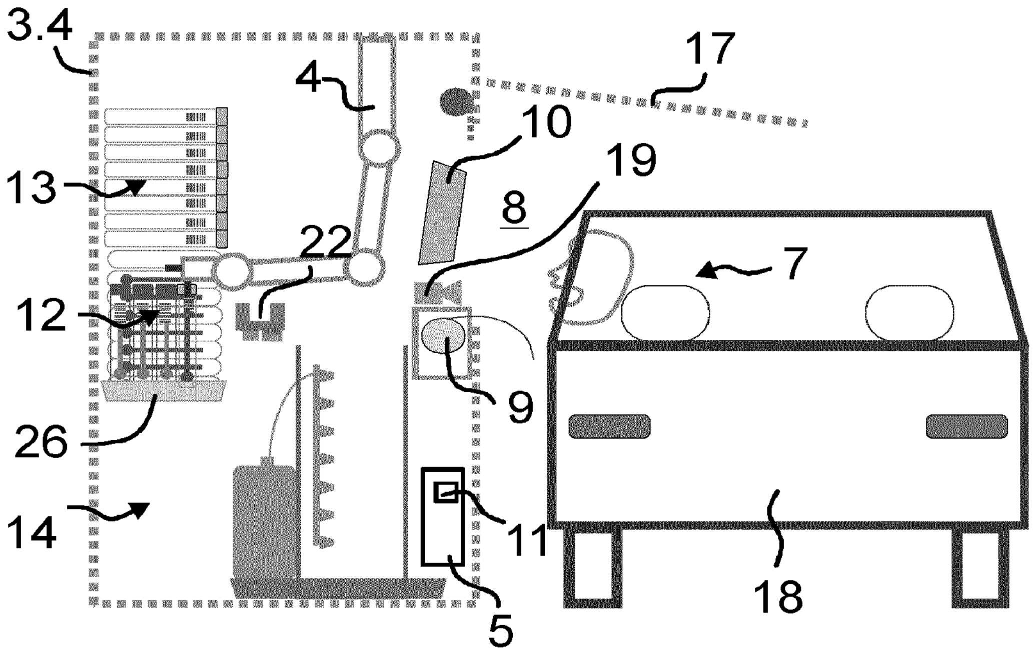
Figure 13:
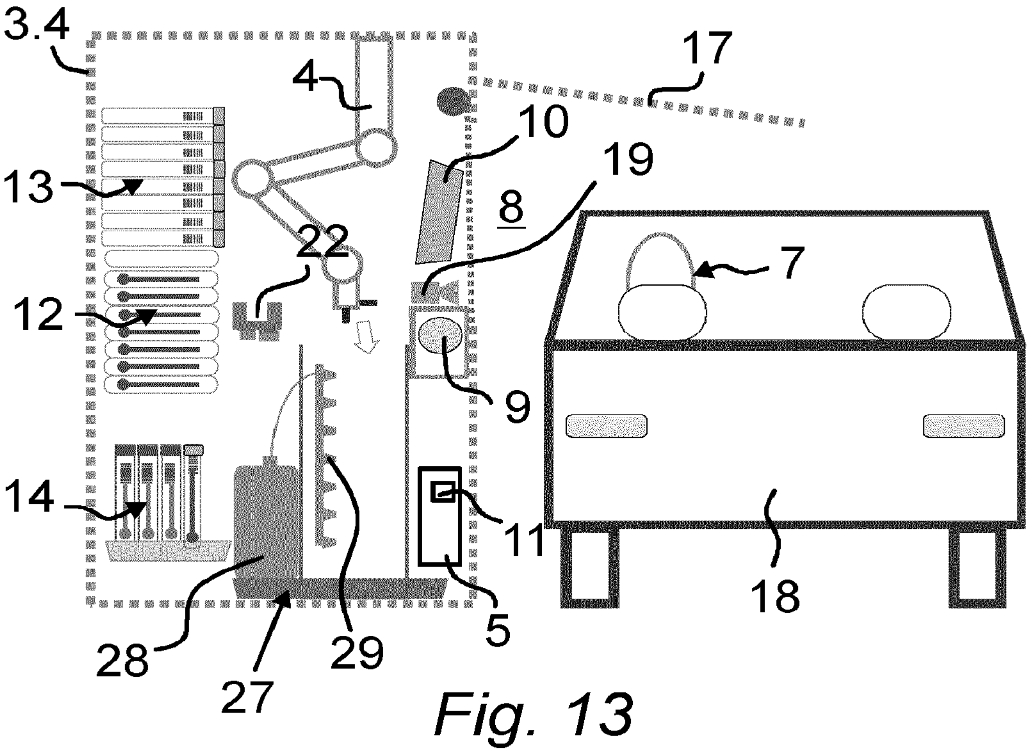
Figure 14:
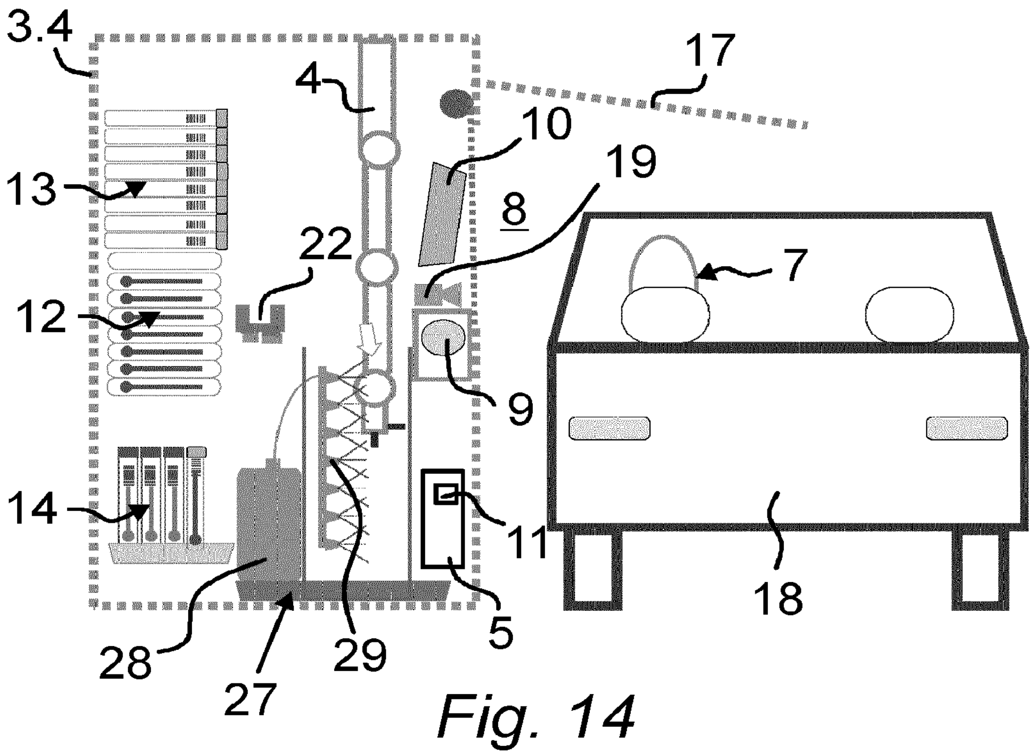
Figure 15:
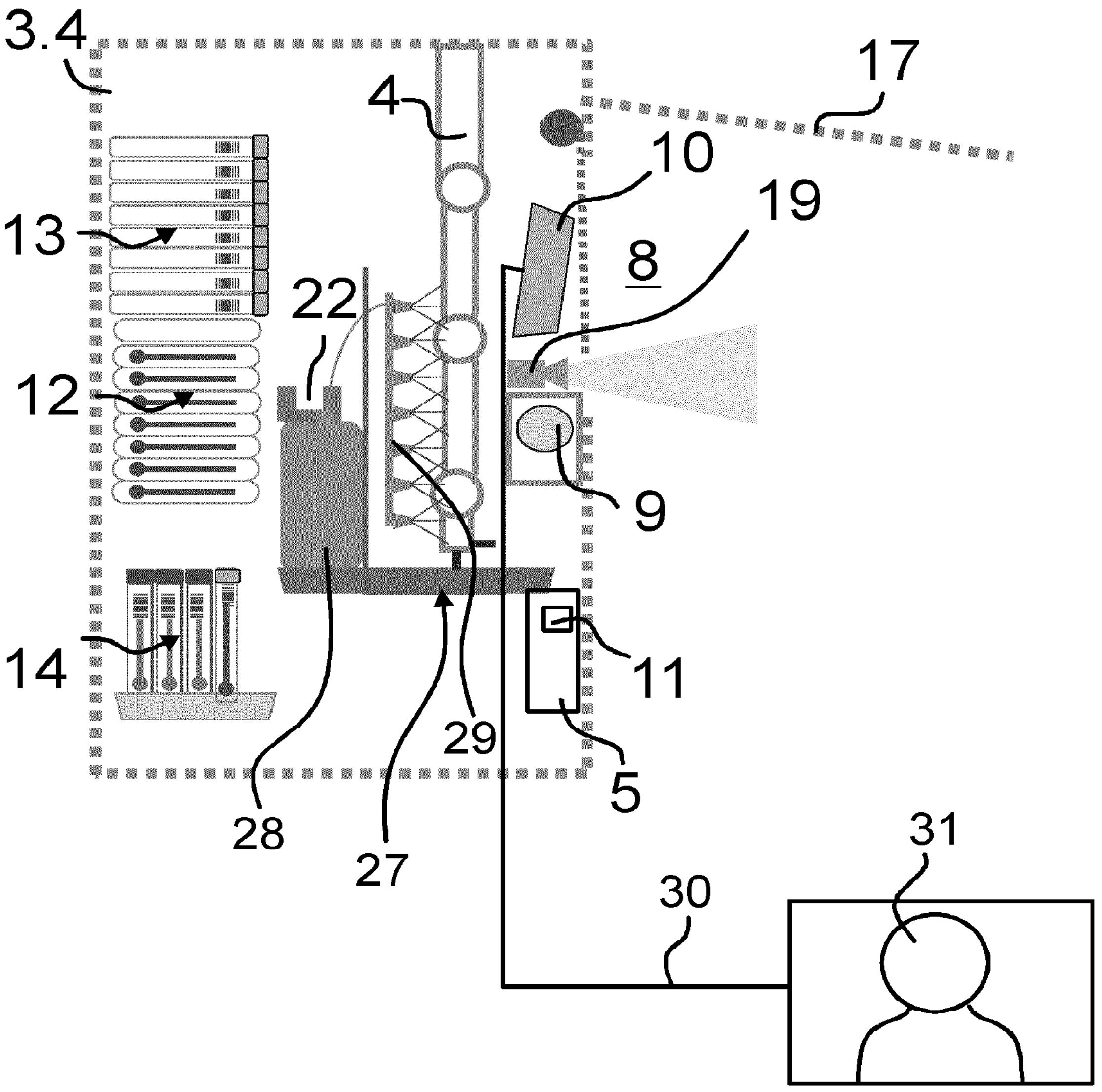

In both cases, the sample carrier 12 together with the removed sample 12*a* is subsequently automatically inserted into the individual sample container 13 by the robot 4 and the individual sample container 13 is closed in a sterile manner, as indicated in FIG. 10. Then the closed individual sample container 13 with the sample carrier 12 and sample 12*a* contained therein is automatically removed from the holder 22 by the robot 4 and stored in a sample magazine 26. The sample magazine 26 can, for example, be automatically stored in a height-adjustable manner within the mobile health test system 3.4 in such a manner that the sample magazine 26 can be automatically moved from its storage position (FIG. 11) to a pick-up position (FIG. 12), where the robot 4 can automatically store the closed individual sample container 13 with the sample carrier 12 and the sample 12*a* contained therein in the sample magazine 26. The sample magazine 26 can be retrieved from the mobile health test system 3.4 by means of a transport unit, such as a vehicle, and brought, for example, in batches to the stationary laboratory 15 (FIG. 1), where a laboratory diagnostic method can also be performed on the samples 12*a* in an automated manner.

After an individual health test has been performed on the person 7, the robot 4 can be disinfected by means of a disinfection device 27. For this purpose, the disinfection device 27 can have a supply 28 of disinfectant, which can be automatically applied to the robot 4 by means of spraying apparatuses 29. The disinfection device 27 can, for example, be automatically height-adjustably mounted within the mobile health test system 3.4 in such a manner that the disinfection device 27 can be automatically moved from its storage position (FIG. 13, FIG. 14) to a treatment position (FIG. 15) where the robot 4 can be sprayed with disinfectant, in particular completely.

Accordingly, the mobile health test system 3.4 may have a disinfection device 27 designed and configured to disinfect the at least one robot 4 of the mobile health test system 3.4.

The output terminal 10 of the mobile health test system 3.4 may form, for example, through its screen and/or speaker, an audio and/or video communication interface 30 (FIG. 15) designed and configured to enable communication between the person 7 located in the counter area 8 of the mobile health test system 3.4 and a service person 31 located remotely from the mobile health test system 3.4.

Figure 16:
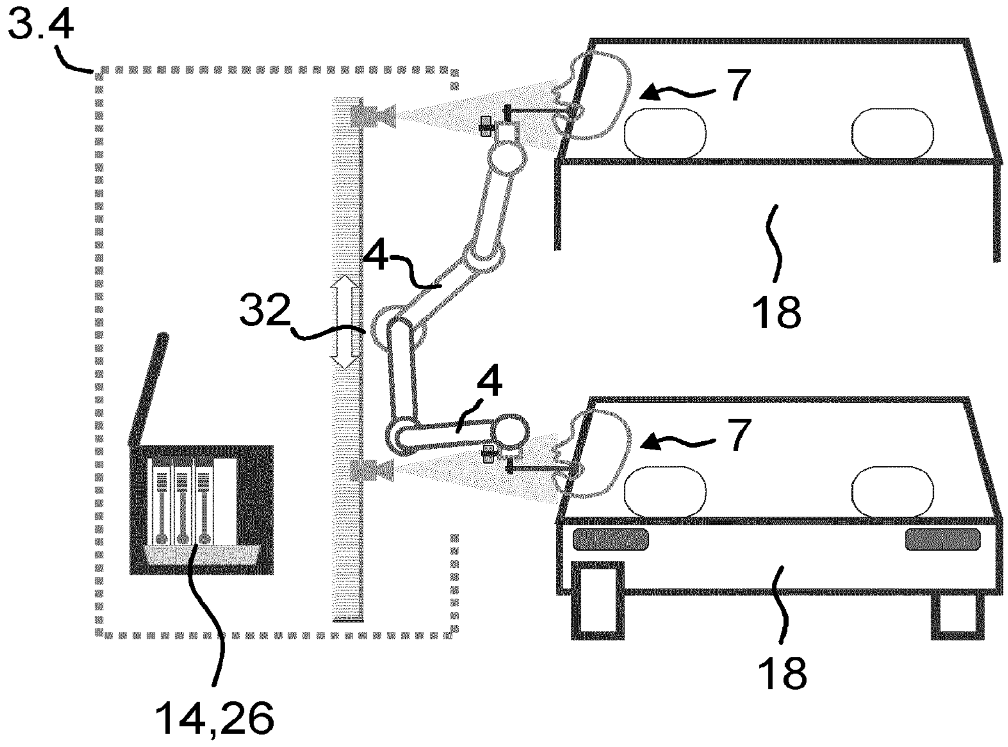

As illustrated in FIG. 16, the robot 4 can also be automatically height-adjustable, for example by means of a linear axis 32, so that the person 7 can be automatically treated at different heights. This may be necessary, for example, depending on the design or size of the vehicle used to approach the mobile health test system 3.4.

While the present invention has been illustrated by a description of various embodiments, and while these embodiments have been described in considerable detail, it is not intended to restrict or in any way limit the scope of the appended claims to such de-tail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

What is claimed is:

1. A method for performing health tests and collecting health-related personal data using resources connected via a computer network, the resources including:

a health database system communicating with the computer network and including a database management system and a personal database, and a plurality of mobile health test systems, each mobile health test system having at least one automatically controllable robot configured to perform at least one health-related test procedure, and a test system controller communicating with the computer network via a first communication means, the method comprising:

collecting personal data via the database management system, wherein the collected personal data includes personal location information of individuals stored in the personal database of the health database system;

deploying at least one mobile health test system to a location based on the personal location information accumulated for several of the individuals;

automatically sending information about an individualized on-site appointment at the deployed location of the at least one mobile health test system to a plurality of the individuals for which the personal location information has been accumulated;

configuring the at least one deployed mobile health test system to perform the at least one health-related test procedure on at least one of the individuals to whom the individualized on-site appointment is assigned during the scheduled time period of the individualized on-site appointment;

performing a laboratory diagnostic method to collect individualized test results from the individual health-related test procedures; and storing the individualized test results in the form of health-related personal data in the personal database of the health database using the database management system.

2. A method for performing health tests and collecting health-related personal data using resources connected via a computer network, the resources including:

a health database system communicating with the computer network and including a database management system and a personal database, and a plurality of mobile health test systems, each mobile health test system having at least one automatically controllable robot configured to perform at least one health-related test procedure, and a test system controller communicating with the computer network via a first communication means, the method comprising:

collecting personal data via the database management system, wherein the collected personal data includes personal location information of individuals stored in the personal database of the health database system;

deploying at least one mobile health test system to a location based on personal location information accumulated for several persons;

automatically sending information about an individualized on-site appointment at the deployed location of the at least one mobile health test system to a plurality of persons;

configuring the at least one deployed mobile health test system to perform the at least one health-related test procedure on at least one of the persons to whom the individualized on-site appointment is assigned during the scheduled time period of the individualized on-site appointment;

performing a laboratory diagnostic method to collect individualized test results from the individual health-related test procedures; and storing the individualized test results in the form of health-related personal data in the personal database of the health database using the database management system;

wherein the personal location information of individuals includes information that has been entered into the personal database via terminal devices connected to the computer network.

3. The method of claim 1, further comprising at least one of:

automatically sending by the database management system information related to individualized test results to an individual person via second communication means; or automatically sending by the database management system anonymized data from multiple test results of multiple persons to a statistics database connected to the database management system via third communication means.

4. The method of claim 1, further comprising:

controlling the at least one automatically controlled robot using the test system controller such that the robot automatically performs the at least one health-related test procedure.

5. The method of claim 4, wherein:

the at least one health-related test procedure comprises a swab from the nose or throat or oral cavity of a person using a sterile sample carrier; and the method further comprises automatically guiding the sterile sample carrier by the robot of the mobile health test system, controlled by the test system controller in at least one of a force-controlled or torque-controlled operation of the robot.

6. The method of claim 1, further comprising:

temporarily storing a plurality of individually assigned samples obtained from the tested persons during the performed health-related test methods in a sample magazine of the mobile health test system.

7. The method of claim 6, further comprising at least one of:

collecting a batch of the plurality of samples from the mobile health test system for transport to a stationary laboratory; or performing a respective laboratory diagnostic procedure on the plurality of samples.

8. The method of claim 1, wherein the test system controller is configured to automatically perform at least one of a health test or a laboratory diagnostic procedure in the mobile health test system using the robot.

9. The method of claim 1, wherein the test system controller is configured to automatically perform a personal authorization of a person at the mobile health test system based on data from the personal database of the health database system before the individual health-related test method is performed on the person at the mobile health test system.

10. A mobile health test system, comprising:

a counter area configured such that persons can contact at least one test apparatus of the mobile health test system;

the at least one test apparatus, comprising:

at least one input terminal, and at least one output terminal;

at least one automatically controllable robot configured to automatically perform at least one sub-step of a health-related test procedure on a person positioned proximate the counter area;

a test system controller; and a transmitting and receiving device configured to connect the test system controller via a first communication means to a computer network such that, in a connected state, personal data can be retrieved from, and written to, a personal database of a health database system connected to the computer network;

the test system controller configured to perform a health-related test procedure using the at least one robot, taking into account the personal data of a person located in the counter area of the mobile health test system and the at least one sub-step that the at least one robot automatically performs during the performance of the health-related test procedure;

wherein the mobile health test system is configured to:

automatically send information about an individualized on-site appointment at a deployed location of the mobile health test system to a plurality of persons, and perform the at least one health-related test procedure on at least one of the plurality of persons to whom the individualized on-site appointment is assigned during a scheduled time period of the individualized on-site appointment.

11. The mobile health test system of claim 10, further comprising a disinfection device configured to disinfect the at least one robot of the mobile health test system.

12. The mobile health test system of claim 10, further comprising:

at least one communication interface configured to enable at least one of audio or video communication between a person located in the counter area of the mobile health test system and a service person located remotely from the mobile health test system.

13. The mobile health test system of claim 10, wherein the mobile health test system is configured to:

automatically send information about an individualized on-site appointment at a deployed location of the mobile health test system to a plurality of persons; and perform the at least one health-related test procedure on at least one of the plurality of persons to whom the individualized on-site appointment is assigned during a scheduled time period of the individualized on-site appointment.

14. The mobile health test system of claim 10, wherein the deployed location of the mobile health test system is based on personal location information accumulated for several persons.

15. The method of claim 1, wherein at least one of:

the resources connected via the computer network include a plurality of terminal devices that are connected to the computer network via second communication means; or automatically sending information about an individualized on-site appointment to at least one person comprises sending the information to the person's individual terminal device.

* * * * *